US009650682B2

(12) United States Patent
Spormann et al.

(10) Patent No.: US 9,650,682 B2
(45) Date of Patent: May 16, 2017

(54) METHODS OF IDENTIFYING AND CLASSIFYING ORGANOHALIDE-RESPIRING BACTERIA

(71) Applicant: The Board of Trustees of the Leland Stanford Junior University, Palo Alto, CA (US)

(72) Inventors: Alfred M. Spormann, Stanford, CA (US); Ian Philip George Marshall, Aarhus C (DK)

( * ) Notice: Subject to any disclaimer, the term of this patent is extended or adjusted under 35 U.S.C. 154(b) by 486 days.

(21) Appl. No.: 14/088,971

(22) Filed: Nov. 25, 2013

(65) Prior Publication Data

US 2014/0148346 A1 May 29, 2014

Related U.S. Application Data

(60) Provisional application No. 61/731,038, filed on Nov. 29, 2012.

(51) Int. Cl.
*C12Q 1/68* (2006.01)

(52) U.S. Cl.
CPC .................................. *C12Q 1/689* (2013.01)

(58) Field of Classification Search
USPC ............................. 435/6.12, 91.2; 536/24.33
See application file for complete search history.

(56) References Cited

U.S. PATENT DOCUMENTS

2010/0279384 A1* 11/2010 Loeffler ............... C12N 9/0004
435/235.1

OTHER PUBLICATIONS

Nucleic acid sequence search report (CP001872 ABFQ01000000 ABFQ01000001-ABFQ01000227).*
Lowe et al. (Nucleic Acid Research, 1990, vol. 18(7)).*
Aulenta, F.; Beccari, M.; Majone, M.; Papini, M. P.; Tandoi, V., Competition for H2 between sulfate reduction and dechlorination in butyrate-fed anaerobic cultures. Process Biochemistry 2008, 43, (2), 161-168.
Aulenta, F.; Majone, M.; Tandoi, V., Enhanced anaerobic bioremediation of chlorinated solvents: environmental factors influencing microbial activity and their relevance under field conditions. Journal of Chemical Technology and Biotechnology 2006, 81, (9), 1463-1474.
Azizian, M. F.; Behrens, S.; Sabalowsky, A.; Dolan, M. E.; Spormann, A. M.; Semprini, L., Continuous-flow column study of reductive dehalogenation of PCE upon bioaugmentation with the Evanite enrichment culture. Journal of Contaminant Hydrology 2008, 100, (1-2), 11-21.
Azizian, M. F.; Marshall, I. P. G.; Behrens, S.; Spormann, A. M.; Semprini, L., Comparison of lactate, formate, and propionate as hydrogen donors for the reductive dehalogenation of trichloroethene in a continuous-flow column. Journal of Contaminant Hydrology 2010, 113, (1-4), 77-92.

Behrens, S.; Azizian, M. F.; McMurdie, P. J.; Sabalowsky, A.; Dolan, M. E.; Semprini, L.; Spormann, A. M. Monitoring abundance and expression of "*Dehalococcoides*" species chloroethene-reductive dehalogenases in a tetrachloroethene-dechlorinating flow column. Appl Environ Microbiol 2008, 74, 5695-5703.
Berggren, D. R. V. Kinetic and Molecular Effects of Sulfate Reduction on a Dechlorinating Culture Under Chemostat Growth Conditions. Masters of Science, Oregon State University, Corvallis, Oregon, 2011.
Boopathy, R.; Peters, R., Enhanced biotransformation of trichloroethylene under mixed electron acceptor conditions. Current Microbiology 2001, 42, (2), 134-138.
Chen, Y.; Cheng, J. J.; Creamer, K. S., Inhibition of anaerobic digestion process: A review. Bioresource Technology 2008, 99, (10), 4044-4064.
Cupples, A. M.; Spormann, A. M.; McCarty, P. L., Vinyl chloride and cis-dichloroethene dechlorination kinetics and microorganism growth under substrate limiting conditions. Environmental Science & Technology 2004, 38, (4), 1102-1107.
Drzyzga, O.; Gerritse, J.; Dijk, J. A.; Elissen, H.; Gottschal, J. C., Coexistence of a sulphate-reducing *Desulfovibrio* species and the dehalorespiring Desulfitobacterium frappieri TCE1 in defined chemostat cultures grown with various combinations of sulphate and tetrachloroethene. Environmental Microbiology 2001, 3, (2), 92-99.
Edgar, R. C., MUSCLE: multiple sequence alignment with high accuracy and high throughput. Nucleic Acids Research 2004, 32, (5), 1792-1797.
Fennell, D. E.; Gossett, J. M., Modeling the production of and competition for hydrogen in a dechlorinating culture. Environmental Science & Technology 1998, 32, (16), 2450-2460.
Gerritse, J.; Drzyzga, O.; Kloetstra, G.; Keijmel, M.; Wiersum, L. P.; Hutson, R.; Collins, M. D.; Gottschal, J. C., Influence of different electron donors and acceptors on dehalorespiration of tetrachloroethene by Desulfitobacterium frappieri TCE1. Applied and Environmental Microbiology 1999, 65, (12), 5212-5221.
Gornall, A. G.; Bardawill, C. J.; David, M. M., Determination of Serum Proteins by Means of the Biuret Reaction. Journal of Biological Chemistry 1949, 177, (2), 751-766.
Granade, S.; Leigh, D. P.; Johnson, C. D.; Chlorinated Solvent Bioremediation: 3 Case Studies, Seventh International In Situ and On-Site Bioremediation Symposium, Orlando, FL, Jun. 2003; Magar, V. S.; Kelley, M. E., Eds. Battelle Press: Orlando, FL; Paper A-13.
He, J. Z.; Ritalahti, K. M.; Yang, K. L.; Koenigsberg, S. S.; Löffler, F. E., Detoxification of vinyl chloride to ethene coupled to growth of an anaerobic bacterium. Nature 2003, 424, (6944), 62-65.
He, J.; Sung, Y.; Krajmalnik-Brown, R.; Ritalahti, K. M.; Löffler, F. E., Isolation and characterization of *Dehalococcoides* sp strain FL2, a trichloroethene (TCE)- and 1,2-dichloroethene-respiring anaerobe. Environmental Microbiology 2005, 7, (9), 1442-1450.
Heimann, A. C.; Friis, A. K.; Jakobsen, R., Effects of sulfate on anaerobic chloroethene degradation by an enriched culture under transient and steady-state hydrogen supply. Water Research 2005, 39, (15), 3579-3586.
Hendrickson, E. R.; Payne, J. A.; Young, R. M.; Starr, M. G.; Perry, M. P.; Fahnestock, S.; Ellis, D. E.; Ebersole, R. C., Molecular analysis of Dehalococcoides 16S ribosomal DNA from chloroethene-contaminated sites throughout North America and Europe. Applied and Environmental Microbiology 2002, 68, (2), 485-495.

(Continued)

*Primary Examiner* — David Thomas
(74) *Attorney, Agent, or Firm* — Thomas | Horstemeyer, LLP (57) ABSTRACT

Briefly described, embodiments of the present disclosure relate to methods and systems for identifying and classifying taxa of organohalide-respiring bacteria, including methods and systems for identify and classify two or more taxa of *Dehalococcoides*.

14 Claims, 4 Drawing Sheets

(56) References Cited

OTHER PUBLICATIONS

Hoelen, T. P.; Reinhard, M., Complete biological dehalogenation of chlorinated ethylenes in sulfate containing groundwater. Biodegradation 2004, 15, (6), 395-403.
Keeling, M. T. Bench-scale study for the bioremediation of chlorinated ethylenes at Point Mugu Naval Air Weapons Station, Point Mugu California, IRP Site 24. Oregon State University, Corvallis, 1998. (uploaded in 2 parts).
Li, W. Z.; Godzik, A., CD-hit: a fast program for clustering and comparing large sets of protein or nucleotide sequences. Bioinformatics 2006, 22, (13), 1658-1659.
Löffler, F. E.; Edwards, E. A., Harnessing microbial activities for environmental cleanup. Current Opinion in Biotechnology 2006, 17, (3), 274-284.
Löffler, F. E.; Tiedje, J. M.; Sanford, R. A., Fraction of electrons consumed in electron acceptor reduction and hydrogen thresholds as indicators of halorespiratory physiology. Applied and Environmental Microbiology 1999, 65, (9), 4049-4056.
Löffler, et al *Dehalococcoides Mccartyi* Gen. Nov., Sp. Nov., Obligate Organohalide-Respiring Anaerobic Bacteria, Relevant to Halogen Cycling and Bioremediation, Belong to a Novel Bacterial Class, Dehalococcoidetes Classis Nov., Within the Phylum Chloroflexi. International Journal of Systematic and Evolutionary Microbiology 2012; DOI 10.1099/ijs.0.034926-0.
Lu, X.-X.; Tao, S.; Bosma, T.; Gerritse, J., Characteristic Hydrogen Concentrations for Various Redox Processes in Batch Study. Journal of Environmental Science and Health, Part A 2001, 36, (9), 1725-1734.
Marshall, I. P. G.; Berggren, D. R. V.; Azizian, M. F.; Burow, L. C.; Semprini, L.; Spormann, A. M., The Hydrogenase Chip: a tiling oligonucleotide DNA microarray technique for characterizing hydrogen-producing and -consuming microbes in microbial communities. Isme Journal 2012, 6, (4), 814-826.
Maymo-Gatell, X.; Chien, Y. T.; Gossett, J. M.; Zinder, S. H., Isolation of a bacterium that reductively dechlorinates tetrachloroethene to ethene. Science 1997, 276, (5318), 1568-1571.
Mazur, C. S.; Jones, W. J., Hydrogen concentrations in sulfate-reducing estuarine sediments during PCE dehalogenation. Environmental Science & Technology 2001, 35, (24), 4783-4788.
McMurdie, P. J.; Behrens, S. F.; Müller, J. A.; Goke, J.; Ritalahti, K. M.; Wagner, R.; Goltsman, E.; Lapidus, A.; Holmes, S.; Löffler, F. E.; Spormann, A. M., Localized Plasticity in the Streamlined Genomes of Vinyl Chloride Respiring Dehalococcoides. Plos Genetics 2009, 5, (11).
Muyzer, G.; de Waal, E. C.; Uitterlinden, A. G. Profiling of complex microbial populations by denaturing gradient gel electrophoresis analysis of polymerase chain reaction-amplified genes coding for 16S rRNA. Appl Environ Microbiol 1993, 59, 695-700.
Muyzer, G.; Stams, A. J. M., The ecology and biotechnology of sulphate-reducing bacteria. Nat. Rev. Micro. 2008, 6, (6), 441-454.
Pang, I. J. Microcosm Study of Enhanced Biotransformation of Vinyl Chloride to Ethylene with TCE Additions Under Anaerobic Conditions from Point Mugu, California. Oregon State University, Corvallis, 2000. (uploaded in 2 parts).
Sleep, B. E.; Seepersad, D. J.; Mo, K.; Heidorn, C. M.; Hrapovic, L.; Morrill, P. L.; McMaster, M. L.; Hood, E. D.; LeBron, C.; Sherwood Lollar, B.; Major, D. W.; Edwards, E. A., Biological Enhancement of Tetrachloroethene Dissolution and Associated Microbial Community Changes. Environmental Science & Technology 2006, 40, (11), 3623-3633.
Smits, T. H. M.; Devenoges, C.; Szynalski, K.; Maillard, J.; Holliger, C. Development of a real-time PCR method for quantification of the three genera *Dehalobacter*, *Dehalococcoides*, and *Desulfitobacterium* in microbial communities. J Microbiol Methods 2004, 57, 369-378.
Townsend, G. T.; Suflita, J. M., Influence of sulfur oxyanions on reductive dehalogenation activities in Desulfomonile tiedjei. Applied and Environmental Microbiology 1997, 63, (9), 3594-3599.
Yu, S. H.; Dolan, M. E.; Semprini, L., Kinetics and inhibition of reductive dechlorination of chlorinated ethylenes by two different mixed cultures. Environmental Science & Technology 2005, 39, (1), 195-205.

* cited by examiner

METHODS OF IDENTIFYING AND CLASSIFYING ORGANOHALIDE-RESPIRING BACTERIA

CROSS-REFERENCE TO RELATED APPLICATION

This application claims priority to and the benefit of U.S. provisional patent application entitled "Methods of Identifying and Classifying Organohalide-respiring Bacteria", Ser. No. 61/731,038 filed Nov. 29, 2012 and incorporated herein by reference in its entirety.

STATEMENT OF GOVERNMENTAL SUPPORT

This invention was made with government support under contract W912HQ-07-C-0045, awarded by the Department of the Army. The government has certain rights in the invention.

BACKGROUND

Chlorinated organic compounds, including tetrachloroethene (PCE) and trichloroethene (TCE), are the most common groundwater contaminants in the United States. These contaminants are also found in soil and sediment at contamination sites. These compounds were commonly used as solvents, dry cleaning agents, and engine degreasers for much of the $20^{th}$ century and have become some of the most common groundwater contaminants One method of cleaning up PCE that has become widely used in recent years is bioremediation via reductive dechlorination. In this process, anaerobic microorganisms respire chlorinated solvents, in the process replacing chlorine atoms bound to the carbon with hydrogen atoms. In this way, each chlorine atom on a toxic compound like PCE can be converted to a hydrogen atom in a stepwise process, converting the toxic PCE into relatively harmless ethene.

Some of the organisms most often responsible for carrying out this reductive dechlorination are organohalide-respiring bacterial species, such as species within the genus *Dehalococcoides*. *Dehalococcoides* is particularly notable for its ability to dechlorinate certain contaminants that other microorganisms cannot, for example vinyl chloride. However, different strains of *Dehalococcoides* have been shown to dechlorinate different compounds, as well as being affected by certain environmental parameters to different extents.

An increasing number of environmental consultants offer commercial bioremediation services involving the stimulation of organohalide-degrading bacteria (biostimulation) and/or augmentation of organohalide-degrading bacteria at contaminated sites. However, identification of optimal bioremediation strategies at each site can be challenging, and the efficiency and success of the bioremediation depends on the microbial population at the remediation site and in any microbial cultures used to stimulate or augment the microbial community at the site. Current methods of identification of bacterial strains in mixed microbial communities rely on 16S ribosomal RNA sequencing. Due to high degree of sequence identity between 16S rRNA sequences between strains, it can be difficult to distinguish different strains of organohalide-reducing bacteria within a population.

SUMMARY

Briefly described, the present disclosure provides methods and systems for identifying and classifying taxa of organohalide-respiring bacteria in a sample. In embodiments, methods of identifying and classifying taxa of organohalide-respiring bacteria in a sample includes extracting genomic DNA from bacteria in the sample suspected of containing one or more bacterial organisms capable of reductive dehalogenation of organohalide contaminants; contacting the extracted DNA with a primer pair capable of hybridizing to a conserved region of a gene conserved across a genus of organohalide-respiring bacteria, where the gene is a single copy functional gene and has a sequence identity of about 77.0% to about 99.9% among strains within the genus; amplifying fragments of the gene; and sequencing the gene fragments to identify and classify the taxa of bacteria present in the sample. The present disclosure also includes kits that include a primer pair capable of hybridizing to a conserved region of a gene conserved across a genus of organohalide-respiring bacteria, where the gene is a single copy functional gene and has a sequence identity of about 77.0% to about 99.9% among strains within the genus, and instructions for use of the primer pairs to identifying and classifying taxa of organohalide-respiring bacteria in a sample.

The present disclosure also includes methods and kits for identifying and classifying bacteria from the genus *Dehalococcoides* in a sample including extracting genomic DNA from bacteria in a sample suspected of containing one or more taxa of *Dehalococcoides*; contacting the extracted DNA with a primer pair capable of hybridizing to a conserved region of a gene conserved across *Dehalococcoides*, where the gene is a single copy functional gene and has a sequence identity of between about 77% and 99.9% among strains within *Dehalococcoides*; amplifying fragments of the gene; and sequencing the gene fragments to identify and classify the *Dehalococcoides* bacteria present in the sample into taxa such as, but not limited to, species, strain, and a combination. In embodiments, the gene is an uptake hydrogenase gene (hupL) from *Dehalococcoides*, and in embodiments, the primer pair has the sequences SEQ ID NOs: 1 and 2.

Embodiments of the present disclosure also include methods of assessing the bioremediation potential of a site contaminated with organohalide contaminants by testing a sample from the site to identify and classify the taxa of organohalide-respiring bacteria present in the sample according to the methods of the present disclosure and determining the bioremediation potential of the site based on the identity of organohalide-respiring bacteria present in the sample. The present disclosure also includes methods of monitoring a bioremediation site contaminated with organohalide contaminants by periodically testing a sample from the site during the remediation process to identify and classify the taxa of organohalide-respiring bacteria present in the sample according to the methods of the present disclosure and determining the changes in species and strain diversity of the bacterial organisms from each test period.

Additional methods of the present disclosure include methods of monitoring mixed microbial cultures used for remediation of contaminated sites by periodically testing a sample of the culture to identify and classify the taxa of organohalide-respiring bacteria according to the methods of the present disclosure.

The present disclosure also includes kits including a primer pair capable of hybridizing to a conserved region of uptake hydrogenase gene (hupL) from *Dehalococcoides*, instructions for use of the primer pair to amplify fragments of the hupL gene in genomic DNA extracted from bacteria in a sample suspected of containing one or more taxa of *Dehalococcoides*, and instructions for sequencing the gene fragments to identify and classify the *Dehalococcoides* bacteria present in the sample into taxa selected from species, strain, and a combination thereof.

Other systems, methods, features, and advantages of the present disclosure will be or become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

The disclosure can be better understood with reference to the following drawings, which are discussed in the description and examples below. The components in the drawings are not necessarily to scale, emphasis instead being placed upon clearly illustrating the principles of the present disclosure.

The components in the drawings are not necessarily to scale, emphasis instead being placed upon clearly illustrating the principles of the present disclosure.

DETAILED DESCRIPTION

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, bioengineering, genetics, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions:

In describing and claiming the disclosed subject matter, the following terminology will be used in accordance with the definitions set forth below.

The terms "taxonomic category" or "taxonomic classification" or "classification" as used herein refers to the categorization of organisms into the scientifically established taxonomic categories into which they have been assigned (e.g., kingdom, phylum, class, order, family, genus, species), or, in the case of previously unidentified organisms, the category to which they would likely be assigned according to established scientific procedures based on similarity of genetics or characteristics. The "taxonomic category" may be a, and the act of classification may involve multiple organisms or only one. "Classification" may also involve the act of grouping individuals into categories based on like characteristics, but generally, in the present disclosure "classification" refers to taxonomic classification" unless the context indicates otherwise.

As used herein, the terms "taxon" and "taxa" or "taxonomic category" or "taxonomic classification refer to a group or groups of organisms that have been classified together because they share one or more characteristics that distinguish the group from other such groups. "Classification" according to "taxa" includes categorization of organisms into the scientifically established taxonomic categories into which they have been assigned (e.g., kingdom, phylum, class, order, family, genus, species), or, in the case of previously unidentified organisms, the category to which they would likely be assigned according to established scientific procedures based on similarity of genetics (e.g., sequence identity) or characteristics. Different levels of taxa exist including broad categories (e.g., phylum, class) and a narrower category within the broad categories (e.g., sub-families, genus, species, strains and the like). In the methods of the present disclosure, bacteria are identified and may be classified according to such taxa, at the sub-family, genus, species or strain level.

As used herein, the term "organohalide-respiring bacteria" includes any bacterial organism capable of reductive dehalogenation of organohalide contaminants, such as, but not limited to percholorethylene (PCE), trichloroethene (TCE), vinyl chloride (VC), and other such compounds.

The term "bioremediation site" refers to a site including contaminated soil, groundwater, sediment, or other environmental substrate contaminated with organohalide compounds, where the site has been identified for remediation. Remediation includes the removal and/or reduction of contaminants from the site. "Bioremediation" indicates the contaminants will be removed and/or reduced at least partially by biological methods (e.g., use of microbial organisms capable of de-toxifying such compounds)

As used in the present disclosure, the "bioremediation potential" of a site refers to the perceived ability to successfully decontaminate the site using bioremediation strategies, as assessed by a bioremediation professional. The bioremediation potential is at least partially determined based on the identity and quantity of various taxa of organohalide-respiring bacteria present at the site.

A "bioremediation plan", as used in the present disclosure, refers to a plan for the removal/detoxification of contaminants at a bioremediation site. The bioremediation plan may include a combination of different bioremediation approaches, at least one of which includes the use of organohalide-respiring bacteria to detoxify organohalide compounds.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, singleand double-stranded DNA, DNA that is a mixture of singleand double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

A "gene" typically refers to a hereditary unit corresponding to a sequence of DNA that occupies a specific location on a chromosome and that contains the genetic instruction for a characteristic(s) or trait(s) in an organism.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

A "primer" as used herein generally refers to a nucleic acid strand, or a related molecule, that serves as a starting point for replication, and is used in amplification techniques. Primers are complementary to a segment of a target nucleotide (e.g., DNA, RNA, gene or gene fragment) to be amplified or replicated. Typically primers are used in performing amplification via polymerase chain reaction (PCR). Primers used in such techniques are usually relatively short (generally about 20-50 base pairs), artificially synthesized polynucleotide strands. In PCR, primers are used to select a target polynucleotide sequence to be amplified by the PCR process. A primer hybridizes with (or "anneals" to) the template DNA and is used by the polymerase enzyme as the starting point for the replication/amplification process. By "complementary" is meant that the nucleotide sequence of a primer is such that the primer can form a stable hydrogen bond complex with the template; i.e., the primer can hybridize or anneal to the template by virtue of the formation of base-pairs over a sufficient length consecutive base pairs. The primers herein are selected to be sufficiently complementary to different strands of a particular target DNA sequence to hybridize with their respective strands to initiate replication. Therefore, the primer sequence need not reflect the exact sequence of the template.

A "primer pair" includes a set of two primers, a forward primer and a reverse primer, for amplifying at least a portion of a target gene.

"Sequence identity" or "identity," as used in the present application, is a relationship between two or more nucleotide sequences, as determined by comparing the sequences. In the art, "identity" also refers to the degree of sequence relatedness between the nucleotide sequences as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a nucleotide sequence may be identical to the reference sequence, that is be 100% identical, or it may include up to a certain integer number of base pair alterations as compared to the reference sequence such that the % identity is less than 100%. Such alterations are selected from: at least one deletion, substitution, or insertion, and wherein said alterations may occur at the 5' or 3' positions of the reference nucleotide sequence or anywhere between those terminal positions, interspersed either individually among the base pairs in the reference sequence or in one or more contiguous groups within the reference sequence.

The term "plasmid" as used herein refers to a non-chromosomal double-stranded DNA sequence including an intact "replicon" such that the plasmid is replicated in a host cell.

As used in the present disclosure, the term "clone library" refers to a group of cloned nucleotide sequences obtained from a test sample according to the methods of the present disclosure, where the nucleotides represent full and/or partial copies of genes homologous to a target gene in the group of bacterial organisms to be identified in the sample.

*Dehalococcoides* is a genus of bacteria within class *Dehalococcoidetes* that obtain energy via the oxidation of hydrogen gas and subsequent reductive dehalogenation of halogenated organic compounds Discussion:

Methods of the present disclosure include methods for identifying and classifying taxa of organohalide-respiring bacteria in a sample and methods of assessing and monitoring bioremediation sites and mixed microbial cultures. The chlorinated solvents tetra- and trichloroethene (PCE and TCE, respectively) were used extensively as solvents and degreasers in the past. These, and their reductive dechlorination products, cis-1,2-dichloroethene (cis-DCE) and vinyl chloride (VC), are among the most common groundwater contaminants, are suspected or known carcinogens, and are highly ranked on the priority list of hazardous substances to be addressed through remediation.[2]

The anaerobic bacterial species *Dehalococcoides mccartyi* (*D. mccartyi*) can effectively dechlorinate these chlorinated aliphatic hydrocarbons (CAHs) to ethene, a non-toxic product, via organohalide respiration.[3-5] At least three different major phylogenetic groups (Cornell, Pinellas, and Victoria) of *D. mccartyi* have been identified to date.[6] In-situ bioremediation using these bacteria frequently involves addressing limiting factors to avoid accumulation of cis-DCE or VC.[1] Enhancement options include the bioaugmentation of microbial cultures containing *D. mccartyi* and introducing an electron-donating substrate (typically fermentable organic compounds).[1,7] With substrate addition, the anaerobic reduction of ferric iron or sulfate may be stimulated.[8-13] These competing acceptor reactions can hinder organohalide respiration through competition for electrons or generation of inhibitory products.[9,15,16]

Commercial bioremediation often involves biostimulation and/or bioaugmentation of microbial populations of organohalide-degrading bacteria at contamination sites. The microbial population at a remediation site as well as the population in any microbial cultures used to stimulate or augment the microbial community at the site effects the efficiency and success of the bioremediation. Thus, companies are seeking methods to help identify and classify the species and strains of organohalide-respiring bacteria in the microbial populations at such sites and in such cultures to monitor changes in the populations during the remediation process and to analyze and monitor the quality of the cultures.

A need exists for tools and methods to identify, classify, and/or quantify different taxa (e.g., species and/or strains) of organohalide-respiring bacteria in at least three different areas of the bioremediation industry:

1. To predict whether the microorganisms present at a contaminated site are suitable for reductive dechlorination prior to the investment needed to carry out the bioremediation.
2. To monitor the different taxa of organohalide respiring bacteria present at a contaminated site while reductive dechlorination is happening. For example, interventions that encourage reductive dechlorination often also increase the rate of sulfide production, which could adversely impact the *Dehalococcoides* strains present.
3. To perform quality control on microbial enrichment cultures before these are injected into groundwater to accelerate reductive dechlorination.

Thus, methods of the present disclosure include methods to identify, classify and/or quantify different species and/or strains of organohalide-respiring bacteria present in groundwater, soil samples, and/or enrichment cultures. In embodiments, the organohalide-respiring bacteria identified, classified, and/or quantified in the methods of the present disclosure include, but are not limited to, bacterial species and strains from the genus *Dehalococcoides* and *Chloroflexi*, and combinations of *Dehalococcoides* and *Chloroflex*.

Briefly describe, in embodiments of the methods of the present disclosure, a sample is tested to identify, classify, and/or quantify the bacterial populations in the sample. The sample can be collected from a contamination site (e.g., soil, sediment, and/or groundwater samples from a site), or from enrichment cultures that may be used for biostimulation or bioaugmentation at a bioremediation project. Then, DNA is extracted from bacteria present in the sample using established environmental DNA extraction techniques. The extracted bacterial DNA is amplified (e.g., by PCR) using primers capable of hybridizing with a gene that is conserved across species of a taxa of organohalide respiring bacteria. In embodiments, the gene is a single-copy gene. Then the amplified gene fragments are sequenced in order to determine the identity of the bacteria present and to classify the different bacterial organism into taxa, such as, species and strain. In embodiments, the amplification product can also be used to quantify the amount of different species and/or strains of bacteria present. In embodiments, to identify the bacteria, the PCR amplification product can be ligated into a plasmid and transformed into *E. coli* in order to separate the different sequence types into different clones in a clone library. Then, in embodiments, the different PCR fragments can be Sanger-sequenced and collected in a clone library to construct a sequence alignment and phylogenetic tree with known sequences of the gene to determine the identity of the different types of bacterial organisms in the soil, sediment, groundwater, or enrichment sample.

The methods of the present disclosure for identifying, classifying and/or quantifying different taxa of organohalide-respiring bacteria in a sample can be used for various applications, particularly applications involved in the bioremediation process. In embodiments, the methods of the present disclosure can be used for assessing the bioremediation potential of soil, groundwater, sediment, etc., contaminated with organohalide contaminants, such as but not limited to percholorethylene (PCE), trichloroethene (TCE), vinyl chloride (VC), and other such compounds. Bacterial organisms such as *Dehalococcoides* detoxify many such compounds through reductive dehalogenation, and many different bioremediation strategies center around encouraging the growth and activity of *Dehalococcoides*. Different strains of *Dehalococcoides* possess different physiological characteristics that can affect engineering decisions regarding the best course of action for remediation (e.g., the bioremediation plan), and accurate knowledge about the types or population of *Dehalococcoides* and other organohalide-respiring bacteria present at a site will help engineers assess the bioremediation potential of a site and to create a better bioremediation plan that achieves decontamination in the most efficient and cost-effective manner.

In other embodiments, the methods of the present disclosure can be used for characterization and monitoring of commercially available mixed microbial cultures that contain *Dehalococcoides* and other organohalide respiring bacterial organisms used for the augmentation and stimulation of contaminated sites during remediation. Several companies now offer services augmenting contaminated groundwater with these cultures in order to improve bioremediation. The methods of the present disclosure can be used as a quality control tool to help ensure that the bacterial strains contained in these cultures remain consistent for each customer or, if customized, to ensure that the cultures retain the mixture specified for the customer's site.

Different strains of *Dehalococcoides* have been shown to dechlorinate different compounds, as well as being affected by certain environmental parameters to different extents. For example, the presence of hydrogen sulfide has a negative impact on the growth of certain *Dehalococcoides* strains, and there is evidence that different strains of *Dehalococcoides* are adapted to different concentrations of molecular hydrogen ($H_2$). Thus, in preparing a bioremediation plan for a site, and for maintaining a successful bioremediation, as well as for maintaining cultures for bioremediation, monitoring the identity and/or quantity of different *Dehalococcoides* species and strains present at the site and/or in cultures used for bioremediation stimulation and/or augmentation is useful for successful bioremediation.

In embodiments of the methods of the present disclosure, the gene that is amplified is the uptake hydrogenase gene (hupL). For identification and classification of taxa of bacteria in the *Dehalococcoides* genus, the *Dehalococcoides* hupL gene can be used. Thus, in embodiments, primer pairs are designed from the *Dehalococcoides* hupL gene. Sequencing the hupL gene offers a higher degree of resolving power between different *Dehalococcoides* strains than the 16S rRNA gene that has been typically used in the past. For example, when using 16S rRNA sequences strains BAV1 and CBDB1 are practically indistinguishable (FIG. 1, right) with a difference in sequence identity of around 1.3% (and as close as 0.1% between some strains). However, the resolution is much higher between species and strains when using hupL (FIG. 1, left), with up to a 12% difference in sequences between different *Dehalococcoides* strains.

This approach is also possible with different highly-conserved functional genes in the *Dehalococcoides* genome. The hupL gene was used in the embodiments described in the examples below because it encodes the putative $H_2$ uptake hydrogenase in an organism that is known to grow using $H_2$ alone as its sole food source. It is therefore unlikely that a strain of *Dehalococcoides* would lose hupL where it might lose other functional genes. In embodiments of the present disclosure, primer pairs are used that are capable of hybridizing to the hupL gene in *Dehalococcoides*. In embodiments, one primer pair that can be used in methods of the present disclosure for targeting the uptake hydrogenase gene (hupL) of *Dehalococcoides* is the pair: HupL_F (5'-ATGCAGAAGATAGTAATTGAYC-3') (SEQ ID NO: 1) and HupL_R (5'-GCCAATCTTRAGTTCCATMR-3') (SEQ ID NO: 2).

In embodiments such as described in the examples below, after amplification of the targeted gene sequence by PCR, the sequences from the amplicon mixture are ligated into plasmids and cloned (e.g., in *E. coli* or other suitable organism) to isolate the different amplicons. The plasmid from each clone is then sequenced and the sequences are compared to known sequences (e.g., from a database). Then, the various bacterial species and/or strains can be identified and classified based on sequence identity with database sequences. In embodiments, phylogenetic trees can be made for classification. In other embodiments, a next-generation sequencing platform like 454, Ion Torrent, or Illumina can be used to avoid the need for a cloning step. Various embodiments of the methods of the present disclosure can be contemplated by one of skill in the art within the scope of the present disclosure.

In embodiments of the methods of the present disclosure, the samples tested are from a mixed microbial cultures containing a mixture of taxa (e.g., genus, species, strains) of organohalide-respiring bacterial organisms, or the sample is from a bioremediation site containing organohalide contaminants and suspected of containing one or more bacterial organisms capable of reductive dehalogenation of such organohalide contaminants. In embodiments, the sample may come from a bioremediation site undergoing remediation where cultures of organohalide-respiring bacteria have been added to the site to assist with remediation as part of a bioremediation plan. In embodiments, the sample is selected from soil, groundwater, or sediment from a site contaminated with organohalide compounds.

In embodiments, methods of testing the sample include extracting genomic DNA from bacteria in the sample, contacting the extracted DNA with a primer pair capable of hybridizing to a conserved region of a target gene conserved across a genus of organohalide-respiring bacteria, amplifying fragments of the gene, and sequencing the gene fragments to identify and classify the taxa of bacteria present in the sample. In order to allow for higher resolution identification of individual strains, the sequence identity for the target gene between strains is typically lower than that of many 16SrRNA sequences used in previous methods. However, the target gene used is sufficiently conserved that it is present in each species of the genus and has regions of sufficient conservation to allow design of primer sets that will hybridize to the gene in different species and strains to allow PCR amplification of the gene from the different species and strains. In embodiments, the gene is a single copy functional gene and has a sequence identity of less than 99.9% among strains within the genus. In embodiments, the sequence identity is about 77.0% to about 99.9% among strains within the genus. In other embodiments, the sequence identity is about 80.0% to about 98% among strains within the genus.

The sample can be a mixed microbial culture comprising two or more species of organohalide-respiring bacteria. When the bacteria are classified into taxa, they can be classified to the species level, to the strain level, or a combination of both. While generally the methods of the present disclosure will likely be used to classify bacteria at the species and/or strain level, it is contemplated that in embodiments, the bacterial populations could also be classified to the genus level or higher, if appropriate. In some embodiments of the present disclosure, the bacterial organisms to be identified and classified are from the genus *Dehalococcoides, Chloroflexi*, and/or a combination of these.

The gene or gene fragment used for identification and classification in the methods of the present disclosure (and from which the primers will be derived) can be a gene conserved within a taxa (e.g., a genus) of bacteria. Preferably, it is a single copy gene that is not likely to be lost across the genome and that has a conserved area within the gene for use in designing a primer pair capable of hybridizing across various taxa. But, ideally, the target gene also has a sequence identity that allows for distinction between different strains within a species/genus. For instance, a conserved gene with sequence identity of about 77.0% to about 99.9% among strains within the genus would be useful in the methods of the present disclosure. In embodiments, the sequence identity is about 77.0% to about 99.9% among strains within the genus. In other embodiments, the sequence identity is between about 80.0% and about 98% among strains within the genus. In embodiments the gene is an uptake hydrogenase gene (hupL). In embodiments of the present disclosure, the gene is hupL from *Dehalococcoides*. In some embodiments, the primer pair is a forward and reverse primer for hupL from *Dehalococcoides*. In embodiments, the primer pair includes a forward and reverse primer for hupL from *Dehalococcoides* having SEQ ID NOs: 1 and 2.

Methods of the present disclosure also include monitoring mixed microbial cultures used for remediation of contaminated sites by periodically testing a sample of the culture to identify and classify the taxa of organohalide-respiring bacteria according to the methods described above. The present disclosure also includes methods of assessing the bioremediation potential of a site contaminated with organohalide contaminants by testing a sample from the site to identify and classify the taxa of organohalide-respiring bacteria present in the sample according to the methods of the present disclosure and determining the bioremediation potential of the site based on the identity of organohalide-respiring bacteria present in the sample. Methods of the present disclosure for assessing the bioremediation potential of a site also include quantifying the amount of bacteria in each taxa present in the sample and determining the bioremediation potential of the site based on the identity and quantity of organohalide-respiring bacteria present in the sample. The methods of the present disclosure also include making and/or revising a bioremediation plan for the site based on the bioremediation potential of the site as determined by the methods of the present disclosure.

Methods of the present disclosure further include monitoring a bioremediation site contaminated with organohalide contaminants. Such methods include periodically testing a sample from the site during the remediation process to identify and classify the taxa of organohalide-respiring bacteria according to the methods described above, and determining the changes in species and strain diversity of the bacterial organisms from each test period. Then changes can be made to a bioremediation plan for the site based on the changes in species and strain diversity determined. In such embodiments, changes to the bioremediation plan can be made such as, but not limited to: addition of bacterial cultures, addition of nutrients, addition of nutrient sources, addition of compounds that affect the viability of certain species or strains of the bacterial species or strains identified at the site, and combinations of these changes. Some compounds that can affect the viability of certain species or strains include, but are not limited to: sulfate, sulfide, and combinations thereof, as well as microorganisms that affect the amount of sulfate and sulfide in the culture and/or site. Additional details about some embodiments of the methods of the present disclosure are described in the examples below.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

The present example describes a chemostat study where the reductive dehalogenation of PCE was evaluated in the absence and presence of sulfate. This example investigated the interaction between sulfate reduction and strains of *D. mccartyi* under chemostat growth conditions. Two chemostats were inoculated with the Point Mugu culture, which contains strains of *Dehalococcoides mccartyi*. The control chemostat (PM-5L, no sulfate), achieved pseudo-steady-state transformation of PCE to ethene and VC. Sulfate was introduced to the second chemostat (PM-2L). Effective sulfate reduction was achieved 110 days later. PCE dechlorination efficiency decreased following complete sulfate reduction. The decrease was associated with the enrichment of the Cornell group of *D. mccartyi* and decline of the Pinellas group. Long term exposure to sulfides and/or competition for $H_2$ may have been responsible for the community shift. Chemostats were used in this study to achieve controlled conditions for growth.

Background

In the present example, the Point Mugu (PM) dehalogenating culture was maintained under chemostat growth conditions that yielded $H_2$ concentrations in the range of the $H_2$ thresholds. This culture was enriched from the shallow groundwater at Point Mugu Naval Weapons Station, California (PMNWS), where sulfate concentrations range from 34 to 5,500 mg/L (0.4 to 57 mM) due to salt water intrusion.[14] Early batch studies with this enrichment found *D. mccartyi* strains were present, and that the culture's VC transformation rates exhibited a half-saturation coefficient ($K_s$) value of 602 µmol/L, which is in the range reported for the Cornell group of *D. mccartyi*.[25,26] Using clone library analysis, Azizian et al.[24] reported the phylogenetic composition of microbial biofilms on Bio-Sep® beads obtained after the PM culture was bioaugmented to a soil column and fed TCE and fermenting substrates. *D. mccartyi, Geobacter, Desulfitobacterium*, and *Spirochaetes* phylotypes were present.

In 2007, the PM culture was used to inoculate chemostats to permit the microbial community to adjust to the growth conditions of low $H_2$ concentrations (2 to 30 nM) in the absence of sulfate reduction. The present study was initiated 3 years later when sulfate was introduced to one chemostat. Cells were periodically harvested from the chemostats to monitor PCE dechlorination in batch tests or to identify the relative distribution of *D. mccartyi* strains through clone libraries. To effectively monitor all strains of *D. mccartyi* with sufficient accuracy, a new method was developed based on sequencing clone libraries of the large subunit of the [NiFe] uptake hydrogenase, hupL. The hupL method differentiated *D. mccartyi* strains more effectively than existing methods that target the gene encoding 16S ribosomal RNA.

Materials and Methods

Culture: The PM culture originated from a TCE contaminated aquifer with salt water intrusion at PMNWS, where active sulfate reduction, methanogenesis, and TCE dechlorination to cis-DCE and VC were observed.[14] The PM culture was maintained for ten years under batch growth conditions, being fed TCE and butanol as a fermenting electron donor.[25,27] During this enrichment, methanogenesis ceased and the culture developed the ability to dechlorinate PCE completely to ethene.[25] The PM culture was used to inoculate the first chemostat in a series of three identically operated chemostats: PM-I (inoculated April 2007), PM-2L (February 2008), and PM-5L (July 2009). Each successive chemostat was inoculated with culture from the previous chemostat.

Chemostat Operation:

The culture was maintained between 20 and 22° C. in GL-45 Kimax chemostat reactors (nominally 2 L and 5 L for the PM-2L and PM-5L chemostats, respectively) fitted with Teflon caps and PEEK tubing and fittings to allow anoxic transfers. The influent feed was a sterile basal anoxic medium described by Yang and McCarty,[19] adjusted to double the buffering capacity (1 g/L $K_2HPO_3$ and 3 g/L $Na_2CO_3$) and increase total sulfide ($HS^-$ and $H_2S$) to 0.20 mM. Sulfide concentrations in the influent feed ranged from 0.02 to 0.03 mM due to oxidation and/or precipitation of sulfide minerals.

PCE (saturated, 1.12 mM) served as the electron acceptor, and sodium lactate (4.3 mM) was added as a fermentable electron donor. Fermentation of 4.3 mM lactate to acetate can yield 8.6 mM of $H_2$, while reduction PCE (1.12 mM) would require 4.5 mM, thus excess $H_2$ (4.1 mM) may be produced. Sodium sulfate (1 mM) was added to the influent of the PM-2L chemostat after 733 days of operation, with no increase in lactate. Assuming the acetate produced from lactate fermentation is not used for dechlorination or sulfate reduction, competition for $H_2$ was expected as 4 moles of $H_2$ are required for each mole of sulfate reduced.

The chemostats were continuously stirred with 2 inch Teflon stir bars to achieve complete mixing. The feed rates resulted in hydraulic residence times (HRTs) of 50 and 55.5 days for the PM-2L and PM-5L chemostats, respectively. The long HRTs were chosen to avoid cell washout of these slow-growing dechlorinating microorganisms. Aliquots of culture were periodically sampled through PEEK tubing for protein, kinetic, or microbial analysis as described in the SI.

DNA Extraction & Molecular Analysis:

DNA extraction was performed as previously described in Marshall, I. P.; Berggren, D. R.; Azizian, M. F.; Burow, L. C.; Semprini, L.; Spormann, A. M. The Hydrogenase Chip: a tiling oligonucleotide DNA microarray technique for characterizing hydrogen-producing and -consuming microbes in microbial communities. *ISME J* 2012, 6, 814-826 (which is hereby incorporated by reference herein).

Figure 1:
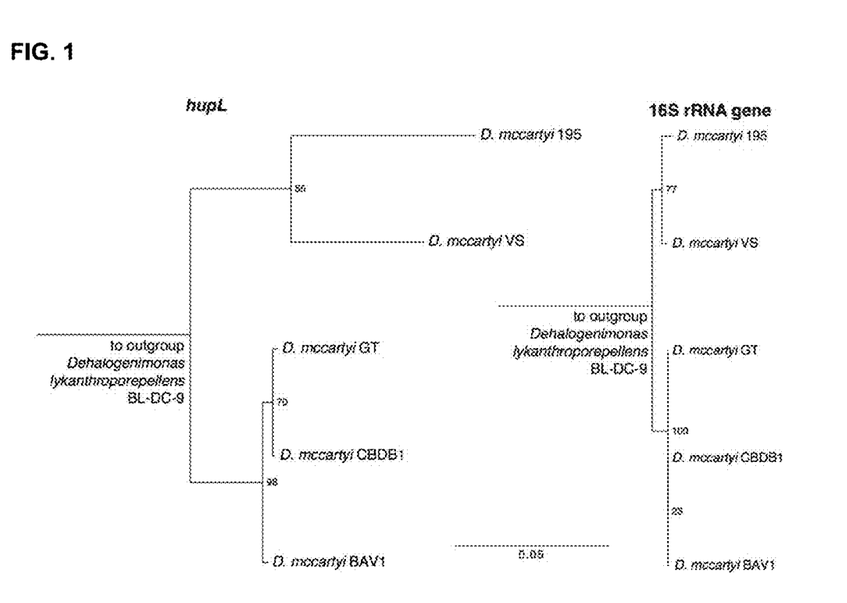
FIG. 1 is an illustration of phylogenetic trees comparing sequence variation of *D. mccartyi* hupL (left) and 16S rRNA genes (right). Branch labels show bootstrap percentages.

Monitoring the strain composition of the *D. mccartyi* community was performed using clone libraries of the gene encoding the putative uptake [NiFe] hydrogenase, hupL. HupL was chosen for analysis as a marker gene for at least the following reasons: (a) it is a single-copy gene in each *D. mccartyi* genome sequenced to date,[32] and therefore will not yield more than one sequence type per strain, (b) it is an essential metabolic gene for all *D. mccartyi*, and therefore will likely be found in all *D. mccartyi* strains, and (c) as a protein-encoding gene, it shows a greater degree of sequence identity variation between *D. mccartyi* strains than the more commonly used 16S rRNA gene (FIG. 1). For the gene analsysis for construction of the phylogenetic trees of FIG. 1, 16SrRNA genes and hupL genes were obtained from their respective genomes via the Integrated Microbial Genomes database (IMG—http://img.jgi.doe.gov/) and aligned using the MUSCLE program. Trees were constructed from the alignments using the PHYML program with default settings and 100× bootstrap. Branch labels show bootstrap percentages. Strains represented by *D. mccartyi* hupL sequence types are not necessarily physiologically identical, but the clone library approach demonstrates general trends in shifting *D. mccartyi* strain composition.

Six hupL clone libraries were processed for the PM-2L chemostat to characterize the shifts that had occurred as the dechlorination abilities of the culture changed. The first sample corresponds to culture collection for inoculation of the PM-5L chemostat (between days 500 and 550), and the second sample on day 727, just prior to sulfate addition. The remaining four samples coincide with the batch kinetic tests performed with PM-2L chemostat culture. Two hupL clone libraries were prepared for the PM-5L chemostat to characterize a long-term steady state observed.

Figure 2:
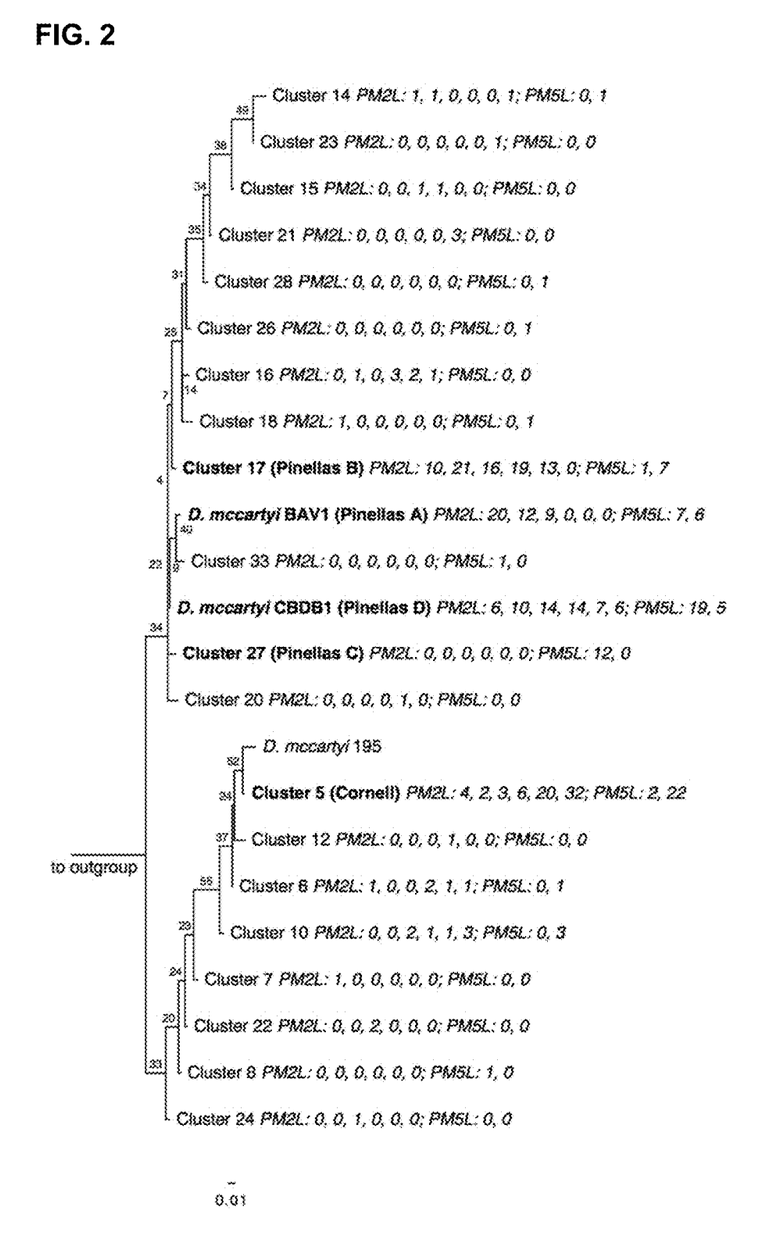
FIG. 2 shows an illustration of a phylogenetic tree of representative sequences from CD-HIT clusters of *D. mccartyi* hupL sequences within the Point Mugu (PM) culture. Numbers following colons show the number of clones for each clone library time point in chronological order, branch labels show bootstrap percentages. Cluster names in bold text are included in FIG. 3A.
Figure 3A:
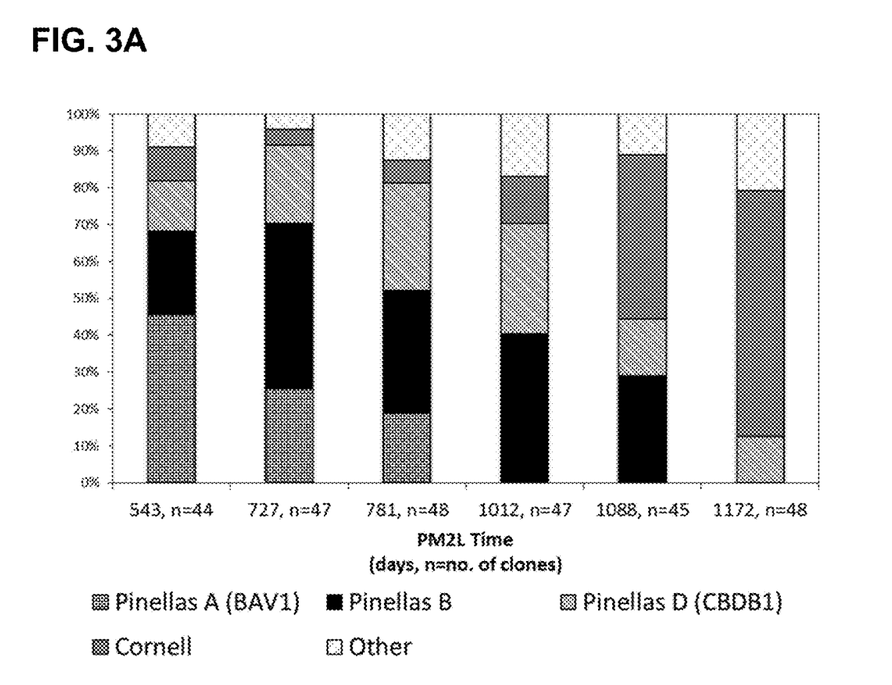
FIGS. 3A and 3B are bar graphs illustrating the composition of the *D. mccartyi* community in the PM-2L (FIG. 3A) and PM-5L (FIG. 3B) chemostat cultures. Each bar indicates the number of hupL clones as a percent of the total *D. mccartyi* hupL clone library at the time the sample was collected. The number of clones analyzed for each sample (n) is provided.
Figure 3B:
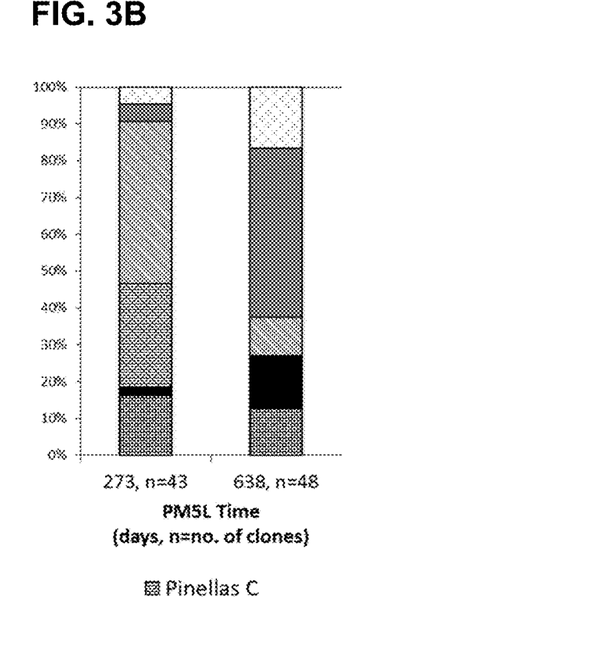

Clones were assigned to clusters using the CD-HIT clustering program[33] at a 99.5% (for *D. mccartyi* hupL) nucleotide identity threshold. Highly identical sequences from genomic databases were included in the CD-HIT input. Representative sequences for each cluster designated by CD-HIT were aligned using the MUSCLE algorithm[34] and their phylogeny reconstructed using the PHYML tree-building algorithm with 100× bootstrap[35] implemented in the Geneious software package (Biomatters, Auckland, New Zealand). *D. mccartyi* strains were classified based on CD-HIT clusters as illustrated in FIG. 2. The abundance of major clusters (more than 10 representatives for at least one time point) is shown in FIG. 3, and remaining clusters are grouped together as "other". hupL were submitted to Genbank and assigned accession numbers JX012186-JX012220.

*Dehalococcoides* hupL Clone Libraries:

Primers HupL_F (5'-ATGCAGAAGATAGTAATT-GAYC-3') (SEQ ID NO: 1) and HupL_R (5'-GCCAATCT-TRAGTTCCATMR-3') (SEQ ID NO: 2) were used for amplification of a 1246 bp fragment of the hupL gene from *Dehalococcoides* sp. Primers were used at a concentration of 0.5 µM each to PCR-amplify hupL in 50 µL reactions with 25 µL 2× DreamTaq Green Master Mix (Thermo Scientific), cycled with an initial 95° C. denaturation step for 3 min, followed by 45 cycles with 30 s at 95° C., 30 s at 55° C., 30 s at 72° C., then a final 72° C. extension step of 10 min.

PCR products were cloned using the TOPO TA cloning kit (Invitrogen) with the pCR2.1-TOPO cloning vector, then Sanger-sequenced using the M13F primer (5'-GTAAAAC-GACGGCCAGT-3) (SEQ ID NO: 3) (Beckman-Coulter Genomics, Danvers, Mass.). Clones were assigned to clusters by using the CD-HIT clustering program at a 99.5% (for *D. mccartyi* hupL) nucleotide identity threshold. Representative sequences for each cluster designated by CD-HIT were aligned using the MUSCLE algorithm[34] and their phyloeny reconstructed using the PHYML tree-building algorithm[35] with 100× bootstrap implemented in the Geneious software package (Biomatters, Auckland, New Zealand). *D. mccartyi* phylotype assignments were made based on CD-HIT clusters as illustrated in FIG. 2.

Results:

Clone Library Analysis of *D. mccartyi* hupL in the Chemostat Cultures:

The relative distribution of *D. mccartyi* strains in each chemostat are displayed in graph form in FIGS. 3A and 3B and as a phylogenetic tree in FIG. 2. Five major clusters were identified: four clusters with a high degree of identity to *D. mccartyi*, CBDB1, GT, and BAV1 and thus designated "Pinellas" clusters A, B, C, and D, and a cluster with high identity to *D. mccartyi* 195 and thus designated "Cornell". Results from analysis of the PM-2L chemostat culture are displayed in FIG. 3A, and results from the PM-5L chemostat are in FIG. 3B. The Pinellas A cluster was dominant in the PM-2L chemostat before the transient stage where $H_2$ concentrations dropped from around 20 to 2 nM (data not shown). As $H_2$ concentrations decreased, Pinellas C and D gained dominance, and Pinellas A eventually fell below the detection limit. Following sulfate addition, the Cornell cluster slowly grew in proportion to the other strains present, making significant increases when VC dechlorination rates decreased following complete sulfate reduction around day 1100.

Two hupL clone libraries were prepared for the PM-5L chemostat culture from samples collected at the beginning and end of the pseudo-steady-states (Stages 5-II and 5-III).

The PM-5L chemostat was inoculated with culture from the PM-2L chemostat having the *D. mccartyi* strain distribution shown in the first bar on the left of FIG. 3A. The PM-5L results show that the Pinellas A cluster was not eliminated from the chemostat with the increase in dechlorinating activity in Stage 5-II, and, although the Cornell cluster increased in proportion to the other clusters in Stage-5-III, this increase was not concurrent with a drop of Pinellas A below the detection limit as was observed in the PM-2L chemostat.

Molecular methods to distinguish among strains of *D. mccartyi* were not available when PM culture was initially enriched in microcosms constructed with aquifer solids and groundwater from PMNWS. The methods of the present disclosure were used in the present example to track changes in microbial community in a long-term reductive dechlorination chemostat experiment. This has shown changes in the dominant *Dehalococcoides* strain from Pinellas A type (BAV1 relative) to Pinellas D type (a CBDB1 relative) to a Cornell type (FIGS. 3A-3B). Approximately 30-50 clones were sequenced for the data at each of those time points. This change in *Dehalococcoides* community composition coincided with an increase in sulfide-production by sulfate-reducing microbes in the enrichment culture. This example indicates that dechlorination performance can be affected by a shift in the *D. mccartyi* community, illustrating the need for methods to analyze the biological makeup of the microbial cultures at work during various stages of bioremediation.

Example 2

Figure 4:
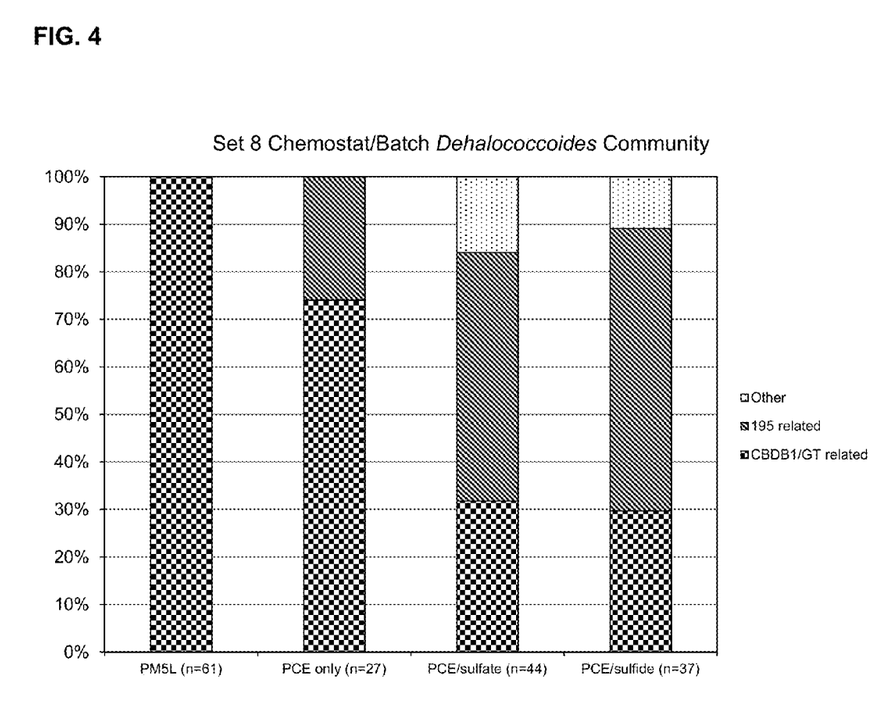
FIG. 4 is a bar graph illustrating the makeup of the *dehalococcoides* community in a chemostat free of sulfate (PM5L), and three different batch cultures derived from that chemostat with addition of PCE or a combination of PCE and sulfate or sulfide.

A subsequent experiment showed that a similar effect to that described in Example 1, above, could be replicated in batch cultures by the addition of sulfate or sulfide, suggesting that the CBDB1/GT-related organism is sensitive to hydrogen sulfide. In this example, three batch reactions were started using material from the PM5L chemostat (described in Example 1, above). One reactor was amended solely with 15 μmol PCE, another with 15 μmol PCE and 16 μmol sulfate, and another with 15 μmol PCE and 4.6 μmol sodium sulfide. The reactors were incubated for 47 days. RNA was then extracted from the cultures and from the PM5L chemostat (from a t=0 sample at the same time as material for the batch reactors) before being analyzed as described in the above example. Results are illustrated in FIG. 4. In this case, the change in *Dehalococcoides* community structure was important knowledge, as the addition of sulfate or sulfide also negatively impacted the microbial community's ability to reduce vinyl chloride. The ability to obtain this type of data on the response of *Dehalococcoides* microbial communities to various changes in environmental conditions could be very useful to practitioners of bioremediation.

References, each of which are incorporated by reference herein.

(1) Löffler, F. E.; Edwards, E. A., Harnessing microbial activities for environmental cleanup. *Current Opinion in Biotechnology* 2006, 17, (3), 274-284.

(2) CERCLA 2007 Priority List Support Document; http://www.atsdr.cdc.gov/cercla/supportdocs/appendix-a.pdf (3) Löffler, F. E.; Yan, J.; Ritalahti, K. M.; Adrian, L.; Edwards, E. A.; Konstantinidis, K. T.; Müller, J. A.; Fullerton, H.; Zinder, S. H.; Spormann, A. M., *Dehalococcoides Mccartyi* Gen. Nov., Sp. Nov., Obligate Organohalide-Respiring Anaerobic Bacteria, Relevant to Halogen Cycling and Bioremediation, Belong to a Novel Bacterial Class, *Dehalococcoidetes* Classis Nov., Within the Phylum *Chloroflexi*. *International Journal of Systematic and Evolutionary Microbiology* 2012; DOI 10.1099/ijs.0.034926-0

(4) MaymoGatell, X.; Chien, Y. T.; Gossett, J. M.; Zinder, S. H., Isolation of a bacterium that reductively dechlorinates tetrachloroethene to ethene. *Science* 1997, 276, (5318), 1568-1571.

(5) He, J. Z.; Ritalahti, K. M.; Yang, K. L.; Koenigsberg, S. S.; Löffler, F. E., Detoxification of vinyl chloride to ethene coupled to growth of an anaerobic bacterium. *Nature* 2003, 424, (6944), 62-65.

(6) Hendrickson, E. R.; Payne, J. A.; Young, R. M.; Starr, M. G.; Perry, M. P.; Fahnestock, S.; Ellis, D. E.; Ebersole, R. C., Molecular analysis of *Dehalococcoides* 16S ribosomal DNA from chloroethene-contaminated sites throughout North America and Europe. *Applied and Environmental Microbiology* 2002, 68, (2), 485-495.

(7) Cupples, A. M.; Spormann, A. M.; McCarty, P. L., Vinyl chloride and cis-dichloroethene dechlorination kinetics and microorganism growth under substrate limiting conditions. *Environmental Science & Technology* 2004, 38, (4), 1102-1107.

(8) Gerritse, J.; Drzyzga, O.; Kloetstra, G.; Keijmel, M.; Wiersum, L. P.; Hutson, R.; Collins, M. D.; Gottschal, J. C., Influence of different electron donors and acceptors on dehalorespiration of tetrachloroethene by *Desulfitobacterium frappieri* TCE1. *Applied and Environmental Microbiology* 1999, 65, (12), 5212-5221.

(9) Aulenta, F.; Pera, A.; Rossetti, S.; Papini, M. P.; Majone, M., Relevance of side reactions in anaerobic reductive dechlorination microcosms amended with different electron donors. *Water Research* 2007, 41, (1), 27-38.

(10) Boopathy, R.; Peters, R., Enhanced biotransformation of trichloroethylene under mixed electron acceptor conditions. *Current Microbiology* 2001, 42, (2), 134-138.

(11) Drzyzga, O.; Gerritse, J.; Dijk, J. A.; Elissen, H.; Gottschal, J. C., Coexistence of a sulphate-reducing *Desulfovibrio* species and the dehalorespiring *Desulfitobacterium frappieri* TCE1 in defined chemostat cultures grown with various combinations of sulphate and tetrachloroethene. *Environmental Microbiology* 2001, 3, (2), 92-99.

(12) Hoelen, T. P.; Reinhard, M., Complete biological dehalogenation of chlorinated ethylenes in sulfate containing groundwater. *Biodegradation* 2004, 15, (6), 395-403.

(13) Heimann, A. C.; Friis, A. K.; Jakobsen, R., Effects of sulfate on anaerobic chloroethene degradation by an enriched culture under transient and steady-state hydrogen supply. *Water Research* 2005, 39, (15), 3579-3586.

(14) Keeling, M. T. Bench-scale study for the bioremediation of chlorinated ethylenes at Point Mugu Naval Air Weapons Station, Point Mugu Calif., IRP Site 24. Oregon State University, Corvallis, 1998.

(15) Fennell, D. E.; Gossett, J. M.; Zinder, S. H., Comparison of butyric kid, ethanol, lactic acid, and propionic acid as hydrogen donors for the reductive dechlorination of tetrachloroethene. *Environmental Science & Technology* 1997, 31, (3), 918-926.

(16) Aulenta, F.; Majone, M.; Tandoi, V., Enhanced anaerobic bioremediation of chlorinated solvents: environmental factors influencing microbial activity and their relevance under field conditions. *Journal of Chemical Technology and Biotechnology* 2006, 81, (9), 1463-1474.

(17) Aulenta, F.; Beccari, M.; Majone, M.; Papini, M. P.; Tandoi, V., Competition for $H_2$ between sulfate reduction and dechlorination in butyrate-fed anaerobic cultures. *Process Biochemistry* 2008, 43, (2), 161-168.

(18) Löffler, F. E.; Tiedje, J. M.; Sanford, R. A., Fraction of electrons consumed in electron acceptor reduction and hydrogen thresholds as indicators of halorespiratory physiology. *Applied and Environmental Microbiology* 1999, 65, (9), 4049-4056.

(19) Yang, Y. R.; McCarty, P. L., Competition for hydrogen within a chlorinated solvent dehalogenating anaerobic mixed culture. *Environmental Science & Technology* 1998, 32, (22), 3591-3597.

(20) Lu, X.-X.; Tao, S.; Bosma, T.; Gerritse, J., Characteristic Hydrogen Concentrations for Various Redox Processes in Batch Study. *Journal of Environmental Science and Health, Part A* 2001, 36, (9), 1725-1734.

(21) Mazur, C. S.; Jones, W. J., Hydrogen concentrations in sulfate-reducing estuarine sediments during PCE dehalogenation. *Environmental Science & Technology* 2001, 35, (24), 4783-4788.

(22) Sleep, B. E.; Seepersad, D. J.; Mo, K.; Heidorn, C. M.; Hrapovic, L.; Morrill, P. L.; McMaster, M. L.; Hood, E. D.; LeBron, C.; Sherwood Lollar, B.; Major, D. W.; Edwards, E. A., Biological Enhancement of Tetrachloroethene Dissolution and Associated Microbial Community Changes. *Environmental Science & Technology* 2006, 40, (11), 3623-3633.

(23) Azizian, M. F.; Behrens, S.; Sabalowsky, A.; Dolan, M. E.; Spormann, A. M.; Semprini, L., Continuous-flow column study of reductive dehalogenation of PCE upon bioaugmentation with the Evanite enrichment culture. *Journal of Contaminant Hydrology* 2008, 100, (1-2), 11-21.

(24) Azizian, M. F.; Marshall, I. P. G.; Behrens, S.; Spormann, A. M.; Semprini, L., Comparison of lactate, formate, and propionate as hydrogen donors for the reductive dehalogenation of trichloroethene in a continuous-flow column. *Journal of Contaminant Hydrology* 2010, 113, (1-4), 77-92.

(25) Yu, S. H.; Dolan, M. E.; Semprini, L., Kinetics and inhibition of reductive dechlorination of chlorinated ethylenes by two different mixed cultures. *Environmental Science & Technology* 2005, 39, (1), 195-205.

(26) Fennell, D. E.; Gossett, J. M., Modeling the production of and competition for hydrogen in a dechlorinating culture. *Environmental Science & Technology* 1998, 32, (16), 2450-2460.

(27) Pang, I. J. Microcosm Study of Enhanced Biotransformation of Vinyl Chloride to Ethylene with TCE Additions Under Anaerobic Conditions from Point Mugu, Calif. Oregon State University, Corvallis, 2000.

(28) Clescerl, L. S.; Greenberg, A. E.; Eaton, A. D. *Standard Methods for the Examination of Water and Wastewater*, Method 4500-$S_2^-$ D, 20$^{th}$ ed.; American Public Health Association, 1999.

(29) Gornall, A. G.; Bardawill, C. J.; David, M. M., Determination of Serum Proteins by Means of the Biuret Reaction. *Journal of Biological Chemistry* 1949, 177, (2), 751-766.

(30) Berggren, D. R. V. Kinetic and Molecular Effects of Sulfate Reduction on a Dechlorinating Culture Under Chemostat Growth Conditions. Masters of Science, Oregon State University, Corvallis, Oreg., 2011.

(31) Marshall, I. P. G.; Berggren, D. R. V.; Azizian, M. F.; Burow, L. C.; Semprini, L.; Spormann, A. M., The Hydrogenase Chip: a tiling oligonucleotide DNA microarray technique for characterizing hydrogen-producing and -consuming microbes in microbial communities. *Isme Journal* 2012, 6, (4), 814-826.

(32) McMurdie, P. J.; Behrens, S. F.; Müller, J. A.; Goke, J.; Ritalahti, K. M.; Wagner, R.; Goltsman, E.; Lapidus, A.; Holmes, S.; Löffler, F. E.; Spormann, A. M., Localized Plasticity in the Streamlined Genomes of Vinyl Chloride Respiring *Dehalococcoides*. *Plos Genetics* 2009, 5, (11).

(33) Li, W. Z.; Godzik, A., Cd-hit: a fast program for clustering and comparing large sets of protein or nucleotide sequences. *Bioinformatics* 2006, 22, (13), 1658-1659.

(34) Edgar, R. C., MUSCLE: multiple sequence alignment with high accuracy and high throughput. *Nucleic Acids Research* 2004, 32, (5), 1792-1797.

(35) Guindon, S.; Gascuel, O., A simple, fast, and accurate algorithm to estimate large phylogenies by maximum likelihood. *Systematic Biology* 2003, 52, (5), 696-704.

(36) Muyzer, G.; Stams, A. J. M., The ecology and biotechnology of sulphate-reducing bacteria. *Nat. Rev. Micro.* 2008, 6, (6), 441-454.

(37) Townsend, G. T.; Suflita, J. M., Influence of sulfur oxyanions on reductive dehalogenation activities in *Desulfomonile tiedjei*. *Applied and Environmental Microbiology* 1997, 63, (9), 3594-3599.

(38) Chen, Y.; Cheng, J. J.; Creamer, K. S., Inhibition of anaerobic digestion process: A review. *Bioresource Technology* 2008, 99, (10), 4044-4064.

(39) He, J.; Sung, Y.; Krajmalnik-Brown, R.; Ritalahti, K. M.; Löffler, F. E., Isolation and characterization of *Dehalococcoides* sp strain FL2, a trichloroethene (TCE)- and 1,2-dichloroethene-respiring anaerobe. *Environmental Microbiology* 2005, 7, (9), 1442-1450.

(40) Granade, S.; Leigh, D. P.; Johnson, C. D.; *Chlorinated Solvent Bioremediation: 3 Case Studies*, Seventh International In Situ and On-Site Bioremediation Symposium, Orlando, Fla., June, 2003; Magar, V. S.; Kelley, M. E., Eds. Battelle Press: Orlando, Fla.; Paper A-13.

(41) Behrens, S.; Azizian, M. F.; McMurdie, P. J.; Sabalowsky, A.; Dolan, M. E.; Semprini, L.; Spormann, A. M. Monitoring abundance and expression of "*Dehalococcoides*" species chloroethene-reductive dehalogenases in a tetrachloroethene-dechlorinating flow column. *Appl Environ Microbiol* 2008, 74, 5695-5703.

(42) Muyzer, G.; de Waal, E. C.; Uitterlinden, A. G. Profiling of complex microbial populations by denaturing gradient gel electrophoresis analysis of polymerase chain reaction-amplified genes coding for 16S rRNA. *Appl Environ Microbiol* 1993, 59, 695-700.

(43) Smits, T. H. M.; Devenoges, C.; Szynalski, K.; Maillard, J.; Holliger, C. Development of a real-time PCR method for quantification of the three genera *Dehalobacter, Dehalococcoides*, and *Desulfitobacterium* in microbial communities. *J Microbiol Methods* 2004, 57, 369-378.

We claim:

1. A method of identifying and classifying bacteria from the genus *Dehalococcoides* in a sample comprising:
   extracting genomic DNA from bacteria in the sample, wherein the sample is a mixed microbial culture comprising two or more taxa of *Dehalococcoides*;
   contacting the extracted DNA with a primer pair capable of hybridizing to a conserved region of a gene conserved across *Dehalococcoides*, where the gene is the uptake hydrogenase gene (hupL) and has a sequence identity of about 80% to about 98% among strains within *Dehalococcoides* and wherein the primer pair has the sequences SEQ ID NO: 1 and 2;
   amplifying fragments of the gene;
   sequencing the gene fragments;
   constructing a sequence alignment with the sequenced fragments and preparing a phylogenetic tree from the sequence alignment to determine the identity of the *Dehalococcoides* bacterial strains in the sample; and
   classifying the *Dehalococcoides* bacteria into taxa selected from the group consisting of: species, strain, and a combination thereof.

2. The method of claim 1, wherein the sample is from a site contaminated with organohalide compounds and wherein the sample is selected from soil, groundwater, or sediment.

3. The method of claim 2 wherein the organohalide compounds are selected from the group consisting of perchloroethylene (PCE), trichloroethene (TCE), vinyl chloride (VC), and a combination of these compounds.

4. The method of claim 1, further comprising: periodically repeating the testing of a subsequent sample of the same mixed microbial culture to identify and classify the taxa of *Dehalococcoides* to monitor changes in species and strain diversity of the mixed microbial culture.

5. The method of claim 1, wherein the bacteria are classified into taxa according to species and strain.

6. The method of claim 1, wherein the gene fragments are amplified with PCR.

7. The method of claim 1, further comprising ligating the amplified gene fragments into a plasmid and making a clone library.

8. The method of claim 7, comprising Sanger-sequencing the gene fragments from the clone library.

9. The method of claim 1, wherein the sample is from a bioremediation site contaminated with organohalide contaminants and wherein the method further comprises: periodically testing additional samples from the site according to the method of claim 1 to identify and classify the taxa of organohalide-respiring bacteria; and determining the changes in species and strain diversity of the bacterial organisms from each test period.

10. The method of claim 9, further comprising: making changes to a bioremediation plan for the site based on the changes in species and strain diversity determined.

11. The method of claim 10, wherein changes to the bioremediation plan are selected from the group consisting of: addition of bacterial cultures, addition of nutrients, addition of nutrient sources, addition of compounds that affect the viability of certain species or strains of the bacterial species or strains identified at the site, and a combination thereof.

12. The method of claim 11, wherein compounds that affect the viability of certain species or strains are selected from the group consisting of sulfate, sulfide, and a combination thereof.

13. The method of claim 1, wherein the sample is from a bioremediation site contaminated with organohalide contaminants and wherein the method further comprises determining the bioremediation potential of the site based on the identity of organohalide-respiring bacteria present in the sample.

14. A method of identifying and classifying bacteria from the genus *Dehalococcoides* in a sample comprising:
 extracting genomic DNA from bacteria in the sample, wherein the sample is a mixed microbial culture comprising two or more taxa of *Dehalococcoides*;
 contacting the extracted DNA with a primer pair capable of hybridizing to a conserved region of an uptake hydrogenase gene (hupL) from *Dehalococcoides* and having the sequences SEQ ID NOs: 1 and 2;
 amplifying fragments of the hupL gene; and
 sequencing the hupL gene fragments; and
 using the sequenced gene fragments to identify and classify the *Dehalococcoides* bacteria present in the sample into taxa selected from the group consisting of: species, strain, and a combination thereof.

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: chemically synthezied Dehalococcoides HupL
      forward primer sequence

<400> SEQUENCE: 1
atgcagaaga tagtaattga yc                                              22

<210> SEQ ID NO 2
<211> LENGTH: 20
<212> TYPE: DNA
<213> ORGANISM: Artificial Sequence
<220> FEATURE:
<223> OTHER INFORMATION: chemically synthezied Dehalococcoides HupL
      reverse primer sequence

<400> SEQUENCE: 2
gccaatcttr agttccatmr                                                 20

<210> SEQ ID NO 3
<211> LENGTH: 17
<212> TYPE: DNA
<213> ORGANISM: Artificial Sequence
<220> FEATURE:
<223> OTHER INFORMATION: chemically synthezied M13 forward primer
      sequence

<400> SEQUENCE: 3
gtaaaacgac ggccagt                                                    17